(12) United States Patent
Kaneumi et al.

(10) Patent No.: US 8,377,188 B2
(45) Date of Patent: *Feb. 19, 2013

(54) POLYFLUOROALKYLPHOSPHONIC ACID OXYALKYLENE ESTER, METHOD FOR PRODUCING THE SAME, AND MOLD-RELEASING AGENT COMPRISING THE SAME AS ACTIVE INGREDIENT

(75) Inventors: Yoshiyama Kaneumi, Ibaraki (JP); Seiichiro Murata, Ibaraki (JP); Katsuyuki Sato, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/395,186

(22) PCT Filed: Sep. 8, 2010

(86) PCT No.: PCT/JP2010/065383
§ 371 (c)(1),
(2), (4) Date: Mar. 9, 2012

(87) PCT Pub. No.: WO2011/030775
PCT Pub. Date: Mar. 17, 2011

(65) Prior Publication Data
US 2012/0180696 A1    Jul. 19, 2012

(30) Foreign Application Priority Data

Sep. 11, 2009 (JP) ................................ 2009-210289
Sep. 11, 2009 (JP) ................................ 2009-210290

(51) Int. Cl.
*B29C 33/60* (2006.01)
*B29C 33/56* (2006.01)
*B28B 7/38* (2006.01)
*C07F 9/40* (2006.01)

(52) U.S. Cl. ........ 106/38.22; 106/2; 106/38.2; 558/204; 562/8; 568/8; 568/14

(58) Field of Classification Search ............. 106/2, 38.2, 106/38.22; 562/8; 568/8, 14; 558/204
See application file for complete search history.

(56) References Cited

U.S. PATENT DOCUMENTS

| | | |
|---|---|---|
| 5,846,516 A | 12/1998 | Riess et al. |
| 8,197,586 B2 * | 6/2012 | Kaneumi et al. ............ 106/38.22 |
| 2011/0315050 A1 * | 12/2011 | Kaneumi et al. ............ 106/38.22 |
| 2012/0077930 A1 * | 3/2012 | Kaneumi et al. ............... 524/612 |
| 2012/0108849 A1 * | 5/2012 | Murata et al. ................... 568/14 |

FOREIGN PATENT DOCUMENTS

| | | |
|---|---|---|
| JP | 52-036588 | 3/1977 |
| JP | 52-039587 | 3/1977 |
| JP | 55-133490 | 10/1980 |
| JP | 58-180597 | 10/1983 |
| JP | 59-166596 | 9/1984 |
| JP | 60-190909 | 9/1985 |
| JP | 60-193615 | 10/1985 |
| JP | 08-199034 | 8/1996 |
| JP | 4506894 B1 * | 5/2010 |
| JP | 2010-235577 | 10/2010 |
| WO | WO 2007/105633 A1 | 9/2007 |

OTHER PUBLICATIONS

International Preliminary Report on Patentability and Written Opinion from corresponding PCT application No. PCT/JP2010/065383 dated Apr. 19, 2012 (5 pgs).
International Search Report from corresponding PCT application No. PCT/JP2010/065383 dated Dec. 7, 2010 (4 pgs).

* cited by examiner

*Primary Examiner* — Anthony J Green
(74) *Attorney, Agent, or Firm* — Brinks Hofer Gilson & Lione

(57) ABSTRACT

Disclosed is a polyfluoroalkylphosphonic acid oxyalkylene ester of the formula: $C_nF_{2n+1}(CH_2CF_2)_a(CF_2CF_2)_b(CH_2CH_2)_cP(O)[O(RO)_mR']_d(OH)_{2-d}$ (RO is a $C_2$-$C_6$ linear or branched oxyalkylene group, R' is a hydrogen atom or a $C_1$-$C_{20}$ alkyl group or aralkyl group, n is 1 to 6, a is 1 to 4, b is 1 to 3, c is 1 to 3, d is 1 or 2, and m is 1 to 100), which is a compound having a perfluoroalkyl group containing 6 or less carbon atoms and referred to as having low bioaccumulation potential, and exhibiting, when used as an active ingredient of a mold-releasing agent, mold release performance equivalent to that of a compound having a perfluoroalkyl group containing 8 or more carbon atoms. This compound is produced by subjecting a polyfluoroalkylphosphonic acid of the formula: $C_nF_{2n+1}(CH_2CF_2)_a(CF_2CF_2)_b(CH_2CH_2)_cP(O)(OH)_2$ and a polyalkyleneglycol or a monoether thereof of the formula: $HO(RO)_mR'$ to a condensation reaction.

19 Claims, No Drawings

POLYFLUOROALKYLPHOSPHONIC ACID OXYALKYLENE ESTER, METHOD FOR PRODUCING THE SAME, AND MOLD-RELEASING AGENT COMPRISING THE SAME AS ACTIVE INGREDIENT

RELATED APPLICATION

This application is a 35 U.S.C. §371 national phase filing of International Patent Application No. PCT/JP2010/065383, filed Sep. 8, 2010, through which and to which priority is claimed under 35 U.S.C. §119 to Japanese Patent Application Nos. 2009-210289, filed Sep. 11, 2009 and 2009-210290, filed Sep. 11, 2009, the entire disclosures of which are hereby expressly incorporated by reference.

TECHNICAL FIELD

The present invention relates to a polyfluoroalkylphosphonic acid oxyalkylene ester, a method for producing the same, and a mold-releasing agent comprising the same as an active ingredient. More particularly, the present invention relates to a polyfluoroalkylphosphonic acid oxyalkylene ester that can provide a mold-releasing agent having excellent film-forming properties and excellent mold releasability, a method for producing the same, and a mold-releasing agent comprising the same as an active ingredient.

BACKGROUND ART

Currently, silicone oil, wax, talc, mica, tetrafluoroethylene resin, and other mold-releasing agents are used in the molding of polymeric materials, such as plastic materials and rubber materials, using molds. Although silicone oil, wax, etc., have excellent mold releasability, such mold-releasing agents are transferred to molded products, thereby impairing uniform coating properties, secondary processability, and other properties; in addition, durability is not sufficient. As for tetrafluoroethylene resin, the durability of mold release effect and secondary processability are satisfactory; however, it is necessary to perform bake treatment to form a film on the molding surface of a mold in the mold-release process, and the same treatment is required for reprocessing. Consequently, many processes are required.

In order to solve these defects, mold-releasing agents comprising a $C_4$-$C_{20}$ polyfluoroalkyl group-containing phosphate ester as one of their active ingredients are proposed (see Patent Documents 1 to 3). These mold-releasing agents exhibit excellent mold releasability and have a longer mold release life than conventional mold-releasing agents; however, due to the recent trend toward the more complicated shape of molded products, there is a demand for mold-releasing agents having much higher performance.

Meanwhile, polyfluoroalkyl phosphonates are also widely used as starting materials for the synthesis of mold-releasing agents. Compounds having a $C_8$-$C_{12}$ perfluoroalkyl group are most likely to develop mold release performance when used as mold-releasing agents. In particular, phosphonate compounds having a perfluorooctyl group and represented by the general formula:

are preferably used for this kind of application (see Patent Documents 4 to 7).

Incidentally, it is reported that phosphate or phosphonate compounds having a $C_8$-$C_{12}$ perfluoroalkyl group are biologically degraded in the environment and converted to compounds having relatively high bioaccumulation and environmental concentration, causing concerns for exposure during treatment processes, and for release or diffusion from waste, treated substrates, etc., into the environment. Moreover, compounds having a perfluoroalkyl group containing 14 or more carbon atoms are very difficult to handle because of their physical and chemical properties, and hence, such compounds are rarely used in practice.

Furthermore, as for phosphate or phosphonate compounds having a perfluoroalkyl group containing 8 or more carbon atoms, generation and mixing of perfluorooctanoic acids with high bioaccumulation potential is unavoidable during the production of these compounds. For these reasons, companies that produce such phosphate or phosphonate compounds have retreated from the production of the compounds or promoted the use of alternative compounds having a perfluoroalkyl group containing 6 or less carbon atoms.

However, compounds having a perfluoroalkyl group containing 6 or less carbon atoms cause a significant decrease in orientation on the surface of a treated substrate, and the melting point, glass transition point (Tg), etc., of the compounds are markedly lower than those of $C_8$ compounds. Accordingly, the compounds are highly influenced by their environmental conditions, such as temperature, humidity, stress, and contact with organic solvents. Consequently, the desired performance cannot be sufficiently achieved, and durability and other properties are affected.

PRIOR ART DOCUMENT

Patent Document

Patent Document 1: JP-B-53-23270
Patent Document 2: JP-B-53-23271
Patent Document 3: JP-B-57-48035
Patent Document 4: JP-B-2-45572
Patent Document 5: JP-B-3-78244
Patent Document 6: JP-B-4-4923
Patent Document 7: JP-B-4-11366
Patent Document 8: WO 2007/105633 A1

OUTLINE OF THE INVENTION

Problem to be Solved by the Invention

An object of the present invention is to provide a polyfluoroalkylphosphonic acid oxyalkylene ester having a perfluoroalkyl group containing 6 or less carbon atoms, which is said to have low bioaccumulation potential, and exhibiting, when used as an active ingredient of a mold-releasing agent, mold release performance equivalent to that of a compound having a perfluoroalkyl group containing 8 or more carbon atoms; a method for producing the same; and a mold-releasing agent comprising the same as an active ingredient.

Means for Solving the Problem

The present invention provides a polyfluoroalkylphosphonic acid oxyalkylene ester represented by the general formula:

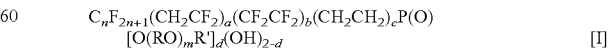

wherein RO is a linear or branched oxyalkylene group having 2 to 6 carbon atoms, R' is a hydrogen atom, an alkyl group having 1 to 20 carbon atoms, or aralkyl group, n is an integer of 1 to 6, a is an integer of 1 to 4, b is an integer of 1 to 3, c is an integer of 1 to 3, d is an integer of 1 or 2, and m is an integer of 1 to 100.

Such a polyfluoroalkylphosphonic acid oxyalkylene ester is produced by subjecting a polyfluoroalkylphosphonic acid represented by the general formula:

$$C_nF_{2n+1}(CH_2CF_2)_a(CF_2CF_2)_b(CH_2CH_2)_cP(O)(OH)_2 \quad [II]$$

and a polyalkyleneglycol or a monoether thereof represented by the general formula:

$$HO(RO)_mR' \quad [X]$$

to a condensation reaction.

The above polyfluoroalkylphosphonic acid oxyalkylene ester [I] according to the present invention is used as an active ingredient of a mold-releasing agent.

Effect of the Invention

When released into the environment, the polyfluoroalkylphosphonic acid oxyalkylene ester of the present invention undergoes HF-elimination in the —$CH_2CF_2$— bonding site of the molecule, and a double bond is formed. The result is then subjected to ozone decomposition etc. to have a structure that is easily decomposed into a compound with low environmental concentration and low bioaccumulation potential. Moreover, the polyfluoroalkylphosphonic acid oxyalkylene ester does not produce environmental loading substances (e.g., perfluoroalkyl carboxylic acids having 8 or more carbon atoms) in the production process thereof.

A mold-releasing agent comprising the polyfluoroalkylphosphonic acid oxyalkylene ester as an active ingredient exhibits effective mold release performance, even when, for example, it is prepared as an aqueous or organic solvent mold-releasing agent having a concentration of about 1.0 wt. % or less, and when it is applied to an object to be subjected to a mold release treatment (e.g., a molding mold). This excellent effect is attributable to the extremely high solubility of the polyfluoroalkylphosphonic acid oxyalkylene ester in solvents. Using this as an active ingredient, a mold-releasing agent having excellent mold releasability can be obtained. Moreover, since this mold-releasing agent exhibits excellent film-forming properties, mold releasability, and durability, mold contamination caused by the mold-releasing agent can be reduced, and the dimensional accuracy of the molded product can be improved.

Furthermore, the molded product does not lead to electrical contact failures, and has excellent secondary vulcanization property.

EMBODIMENTS FOR CARRYING OUT THE INVENTION

The polyfluoroalkylphosphonic acid oxyalkylene ester is produced by subjecting a polyfluoroalkylphosphonic acid represented by the general formula:

$$C_nF_{2n+1}(CH_2CF_2)_a(CF_2CF_2)_b(CH_2CH_2)_cP(O)(OH)_2 \quad [II]$$

and a polyalkyleneglycol or a monoether thereof represented by the general formula:

$$HO(RO)_mR' \quad [X]$$

to a condensation reaction.

The polyfluoroalkylphosphonic acid of the formula:

$$C_nF_{2n+1}(CH_2CF_2)_a(CF_2CF_2)_b(CH_2CH_2)_cP(O)(OH)_2 \quad [II]$$

is produced by the hydrolysis reaction of a polyfluoroalkylphosphonic acid diester represented by the general formula:

$$C_nF_{2n+1}(CH_2CF_2)_a(CF_2CF_2)_b(CH_2CH_2)_cP(O)(OR)_2 \quad [III]$$

wherein R is an alkyl group having 1 to 4 carbon atoms, n is an integer of 1 to 6, a is an integer of 1 to 4, b is an integer of 1 to 3, and c is an integer of 1 to 3.

The polyfluoroalkylphosphonic acid diester [III], which is used as a starting material for this reaction, is obtained by the reaction of a polyfluoroalkyl iodide [IV] of the formula:

$$C_nF_{2n+1}(CH_2CF_2)_a(CF_2CF_2)_b(CH_2CH_2)_cI \quad [IV]$$

with trialkyl phosphite $P(OR)_3$. The polyfluoroalkyl iodide [IV] is a known compound and is disclosed in Patent Document 8.

The polyfluoroalkyl iodide [IV], which is used as a starting material for the synthesis of the polyfluoroalkylphosphonic acid diester [III], is produced by the addition reaction of a terminally iodized compound represented by the general formula:

$$C_nF_{2n+1}(CH_2CF_2)_a(CF_2CF_2)_bI \quad [V]$$

with ethylene. The ethylene addition reaction is carried out in such a manner that the compound [V] is subjected to an addition reaction with pressurized ethylene in the presence of a peroxide initiator. The number of addition is 1 to 3, preferably 1, although depending on the reaction conditions. Although the reaction temperature depends on the degradation temperature of the initiator used, the reaction is generally conducted at about 80 to 120° C.; when a peroxide initiator that decomposes at a low temperature is used, the reaction can be conducted at 80° C. or below.

As a peroxide initiator, tert-butyl peroxide, di(tert-butylcyclohexyl)peroxy dicarbonate, dicetylperoxy dicarbonate, di-n-propylperoxy dicarbonate, diisopropylperoxy dicarbonate, di-sec-butylperoxy dicarbonate, or the like may be used at a ratio of about 1 to 5 mol % with respect to the compound [V], in terms of the progress and controllability of the reaction.

The terminally iodized compound [V] is synthesized through a series of the following steps:
(1) A perfluoroalkyl iodide represented by the general formula:

$$C_nF_{2n+1}I \text{ (n: 1 to 6)}$$

is reacted with vinylidene fluoride in the presence of a peroxide initiator as described above in an amount of about 0.1 to 0.5 mol % based on the starting material compound to obtain a compound represented by the general formula:

$$C_nF_{2n+1}(CH_2CF_2)_aI \quad [VI]$$

(2) The compound represented by the general formula [VI] is reacted with tetrafluoroethylene in the presence of a peroxide initiator to thereby obtain a terminally iodized compound represented by the general formula [V] described above. In the general formula [V], b is an integer of 1 to 3, preferably 1 or 2. The organic peroxide initiator as mentioned above can be used in this reaction in the same amount as in step (1).

Although the reaction temperature of the addition reaction of vinylidene fluoride and tetrafluoroethylene depends on the decomposition temperature of the initiator used, the use of a peroxide initiator that decomposes at a low temperature allows the reaction to occur at 80° C. or less under low-pressure conditions. The reaction is carried out in the following manner. The perfluoroalkyl iodide $C_nF_{2n+1}I$ or the compound [VI] is charged in an autoclave, and the internal temperature is increased to about 10 to 60° C. For example, when the temperature reaches 50° C., a peroxide initiator dissolved in the perfluoroalkyl iodide $C_nF_{2n+1}I$ or the compound [VI] is added thereto. When the internal temperature reaches 55° C., for example, vinylidene fluoride or tetrafluoroethylene is added in batches while maintaining the pressure at about 0.1 to 0.6 MPa. After the desired amount of vinylidene fluoride or tetrafluoroethylene is added in batches, aging is carried out, for example, at a temperature of about 55 to 80° C. for about one hour. The amount of vinylidene fluoride or tetrafluoroethylene added affects the number of vinylidene fluoride skeletons a or tetrafluoroethylene skeletons b added by the reaction. Generally, a mixture of various a values and b values is formed.

The fact that these reactions can be carried out at low temperatures indicates that not only energy usage amount can be reduced, but also corrosion due to hydrofluoric acid etc. in facilities can be prevented, thereby reducing the frequency of updating the facilities. Additionally, since more inexpensive materials can be used, capital investment costs can also be kept low, in addition to the decrease in update frequency.

Specific examples of the compound [V] to which ethylene is added include the following compounds. These compounds are mixtures of oligomers having various a values and b values. Oligomers that have specific a value and b value can be isolated by distilling the mixtures. Oligomers that do not have predetermined a and b values can be reused after isolation or as the mixtures in the reaction of increasing the number of oligomers with vinylidene fluoride or tetrafluoroethylene.

$C_2F_5(CH_2CF_2)(CF_2CF_2)I$ $C_2F_5(CH_2CF_2)(CF_2CF_2)_2I$ $C_2F_5(CH_2CF_2)_2(CF_2CF_2)I$ $C_2F_5(CH_2CF_2)_2(CF_2CF_2)_2I$ $C_4F_9(CH_2CF_2)(CF_2CF_2)I$ $C_4F_9(CH_2CF_2)_2(CF_2CF_2)I$ $C_4F_9(CH_2CF_2)(CF_2CF_2)_2I$ $C_4F_9(CH_2CF_2)_2(CF_2CF_2)_2I$ $C_2F_5(CH_2CF_2)(CF_2CF_2)_3I$ $C_4F_9(CH_2CF_2)(CF_2CF_2)_3I$

The polyfluoroalkyl iodide [IV] prepared by the addition reaction of the compound [V] as described above with ethylene can be reacted with trialkyl phosphite $P(OR)_3$ having an alkyl group containing 1 to 4 carbon atoms, such as trimethyl phosphite, triethyl phosphite, tripropyl phosphite, or tributyl phosphite, to perform the RI-elimination reaction, thereby obtaining a polyfluoroalkylphosphonic acid diester [III], which is used as a starting material. Without the addition reaction of the compound [V] with ethylene, the RI-elimination reaction with trialkyl phosphite does not proceed.

The hydrolysis reaction of the polyfluoroalkylphosphonic acid diester [III] can be readily carried out by stirring at about 90 to 100° C. in the presence of an acid catalyst, such as inorganic acid typified by concentrated hydrochloric acid. The resulting reaction mixture is filtered under reduced pressure, followed by water washing/filtration, acetone washing/filtration, and other methods, thereby obtaining a polyfluoroalkylphosphonic acid [II], which is used as one reaction starting material, with a good yield of 90% or more.

Examples of the polyalkyleneglycol or monoether thereof represented the general formula:

$HO(RO)_mR'$  [X]

which is used as the other reaction starting material, include polyethyleneglycol, polypropyleneglycol, polybutyleneglycol, polyhexyleneglycol, or monoalkyl ether or monoaralkyl ether thereof; preferably, monomethyl ether, monoethyl ether, etc., wherein m is 1 to 100, and the number average molecular weight (Mn) is preferably about 200 to 4,000, are used.

The condensation reaction between the polyfluoroalkylphosphonic acid [II] and the polyalkyleneglycol or monoether thereof [X] is carried out by heating at a temperature of about 80 to 180° C. using a dehydration catalyst, such as concentrated sulfuric acid or concentrated hydrochloric acid. In the reaction, for example, nitrogen bubbling is continuously performed to remove produced water from the reaction system, thereby promoting the dehydration-condensation reaction.

The reaction mixture comprises about 50 wt. % of unreacted polyalkyleneglycol (monoether) and about 50 wt. % of reaction product. The reaction product comprises a mixture of a polyfluoroalkylphosphonic acid monooxyalkylene ester [A] represented by the general formula:

$$C_nF_{2n+1}(CH_2CF_2)_a(CF_2CF_2)_b(CH_2CH_2)_cP(O)[O(RO)_mR'](OH)$$

and a polyfluoroalkylphosphonic acid bis(oxyalkylene) ester [B] represented by the general formula:

$$C_nF_{2n+1}(CH_2CF_2)_a(CF_2CF_2)_b(CH_2CH_2)_cP(O)[O(RO)_mR']_2$$

The polyalkyleneglycol (monoether) [X] is used in an equimolar amount or more based on the polyfluoroalkylphosphonic acid [II]. When the molar ratio is about 2, generally about 1.5 to 2.5, the monooxyalkylene ester [A] is mainly produced; and when the molar ratio is about 4, generally about 3.0 to 4.5, the bis(oxyalkylene) ester [B] is mainly produced.

When a polyalkyleneglycol that is not monoetherified is used, the monooxyalkylene ester [A] or bis(oxyalkylene) ester [B] is mainly produced as well, depending on the molar ratio used. At the same time, a small amount of a product [C] of the following formula in which a polyfluoroalkylphosphonic acid is added by condensation to each of the glycol groups at both ends is also produced.

$$C_nF_{2n+1}(CH_2CF_2)_a(CF_2CF_2)_b(CH_2CH_2)_cP(O)(OH)—O(RO)_m—P(O)(OH)—(CH_2CH_2)_c(CF_2CF_2)_b(CF_2CH_2)_aC_nF_{2n+1}$$

The separation of each of the unreacted polyalkyleneglycol (monoether), polyfluoroalkylphosphonic acid monooxyalkylene ester, and polyfluoroalkylphosphonic acid bis(oxyalkylene) ester from the reaction mixture is performed using preparative liquid chromatography; however, the reaction mixture containing the unreacted polyalkyleneglycol (monoether) can be used as it is in the preparation of mold-releasing agents. Since the unreacted polyalkyleneglycol (monoether) has the effect of reducing the surface tension of water and improving wettability, there is no need to remove the unreacted polyalkyleneglycol (monoether).

The preparation of mold-releasing agents using the polyfluoroalkylphosphonic acid oxyalkylene ester obtained as above is performed by dilution with water or an organic solvent so as to form an aqueous solution, aqueous dispersion, or organic solvent solution in which the solid matters content of the monooxyalkylene ester, bis(oxyalkylene) ester, or mixture thereof is about 0.01 to 30 wt. %, preferably about 0.05 to 3 wt. %.

An example of usable organic solvents is at least one of alcohols, such as methanol, ethanol, n-propanol, and isopropanol; ketones, such as acetone, methyl ethyl ketone, and methyl isobutyl ketone; ethers, such as diethyl ether, diisopropyl ether, dioxane, and tetrahydrofuran; esters, such as ethyl acetate and butyl acetate; polyols or ethers thereof, such as ethyleneglycol, propyleneglycol, diethyleneglycol, triethyleneglycol, tetraethyleneglycol, dipropyleneglycol, tripropyleneglycol, tetrapropyleneglycol, diethyleneglycol monomethyl ether, dipropyleneglycol monomethyl ether, tripropyleneglycol monomethyl ether, and glycerin; polyvalent alcohol derivatives, such as methyl cellosolve, ethyl cellosolve, methyl carbitol, and ethyl carbitol; halogenated hydrocarbons, such as carbon tetrachloride, methylene chloride, trichloroethylene, perchloroethylene, trichloroethane, trichlorofluoromethane, tetrachlorodifluoroethane, trichlorotrifluoroethane, and 1,4-bis(trifluoromethyl)benzene; and the like. Here, the organic solvent can be used in combination with water.

The mold-releasing agent solution may contain the unreacted polyalkylene-glycol or monoether thereof, which is used as a starting material for the synthesis of the polyfluoroalkylphosphonic acid oxyalkylene ester, and may contain, if necessary, amine-based neutralizers, such as triethylamine, triethanolamine, tris(2-hydroxyethyl)amine, and morpholine; various ionic and non-ionic surfactants for improving the wettability of the mold-releasing agent; silicone oil, silicone varnish, etc., for further improving mold releasability and lubricity. The amine-based neutralizer is used in an amount of 0.01 to 3 wt. % based on the total amount of the amine-based neutralizer, polyfluoroalkylphosphonic acid oxyalkylene ester, and water, an organic solvent, or a mixture thereof.

The mold-releasing agent solution can be applied to a mold by any common method, such as dipping, spraying, brushing, aerosol spraying, or impregnated fabric coating. Moreover, examples of molding materials to be molded with a mold to which the mold-releasing agent is applied include polyurethane, polycarbonate, epoxy resin, phenol resin, polyimide resin, vinyl chloride resin, and other resins; natural rubber, chloroprene rubber, fluororubber, and other rubbers.

EXAMPLES

The following describes the present invention with reference to Examples.

Reference Example 1

(1) In a 1-L capacity, four-necked flask equipped with a thermometer and a receiver for removing low-boiling substances, 500 g (0.78 mol) of a compound of the formula: $C_4F_9(CH_2CF_2)(CF_2CF_2)_2(CH_2CH_2)I$ (99 GC %), and 181 g (1.56 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 91 g (0.78 mol) per batch, and the mixture was stirred for 18 hours in total.

After the reaction was completed, the reaction mixture was subjected to simple distillation under reduced pressure at an internal pressure of 0.2 kPa, an internal temperature of 160 to 170° C., and an overhead temperature of 150 to 155° C. The distillate fraction was washed with water, thereby obtaining 412 g (yield: 78%) of a purified reaction product (96 GC %).

The results of $^1$H-NMR and $^{19}$F-NMR confirmed that the resulting purified reaction product was a compound represented by the following formula:

$$C_4F_9(CH_2CF_2)(CF_2CF_2)_2(CH_2CH_2)P(O)(OCH_2CH_3)_2$$

(2) In a 1-L capacity, four-necked flask equipped with a thermometer and a condenser, 300 g (0.44 mol) of the polyfluoroalkylphosphonic acid diester of the formula: $C_4F_9(CH_2CF_2)(CF_2CF_2)_2(CH_2CH_2)P(O)(OCH_2CH_3)_2$ (96 GC %) obtained in step (1) above, and 300 g of about 35% concentrated hydrochloric acid were charged, and the mixture was stirred at 100° C. for 12 hours. After cooling, filtration under reduced pressure was performed to thereby collect 276 g of solid matters. The solid matters were washed with water and filtrated again, further followed by acetone washing and filtration, thereby obtaining 242 g (0.41 mol; yield: 92%) of the target product.

The results of $^1$H-NMR and $^{19}$F-NMR confirmed that the resulting reaction product was the target compound (polyfluoroalkylphosphonic acid A; MW: 592, F content: 61.0 wt. %) represented by the following formula:

$$C_4F_9(CH_2CF_2)(CF_2CF_2)_2(CH_2CH_2)P(O)(OH)_2$$

Example 1

In a 500-ml reaction vessel equipped with a stirrer, a nitrogen bubbling device, and a thermometer, 112 g (0.19 mol) of the polyfluoroalkylphosphonic acid A obtained in Reference Example 1 (2) and 188 g (0.38 mol) of polyethyleneglycol monomethyl ether [PEG-a] (Uniox M-550, produced by NOF Corporation; MW=496, m=about 12) of the formula:

$$HO(CH_2CH_2O)_mCH_3$$

were charged. After the temperature was raised to 70° C., nitrogen bubbling was performed. Thereafter, the internal temperature of the reaction vessel was raised to 155° C., and 1.2 g of concentrated sulfuric acid was added. The reaction was continued for 48 hours while the water produced by the reaction was removed from the reaction system by continuing nitrogen bubbling in the ongoing reaction.

After the completion of the reaction, the resultant was cooled, thereby obtaining 275 g (recovery rate: 92%) of a light yellow wax-like reaction mixture (F content: 22.4 wt. %). The obtained reaction mixture was isolated by preparative liquid chromatography, and the composition of the isolated product was confirmed by $^{19}$F-NMR and $^1$H-NMR. As a result, the weight ratio of PEG-a, product Ia, and product Ib was 50/48/2.

(m=about 12):

$$C_4F_9(CH_2CF_2)(CF_2CF_2)_2(CH_2CH_2)P(O)[O(CH_2CH_2O)_mCH_3](OH) \quad \text{Product Ia}$$

(m=about 12):

$$C_4F_9(CH_2CF_2)(CF_2CF_2)_2(CH_2CH_2)P(O)[O(CH_2CH_2O)_mCH_3]_2 \quad \text{Product Ib}$$

$^{19}$F-NMR; δ=82.0 (3F: $CF_3$—)
−113.1 (4F: —$CF_2CH_2CF_2$—)
−114.5 (2F: —$CF_2CF_2CH_2CF_2$—)
−121.9 to −127.0 (10F: —$CF_2$—)
$^1$H-NMR; δ=1.74 (2H: —$CF_2CH_2CH_2$—)
2.25 (2H: —$CF_2CH_2CH_2$—)
2.90 (2H: —$CF_2CH_2CF_2$—)
3.25 (3H: —$OCH_3$)
3.20 to 3.70 (48H: —$OCH_2CH_2O$—, —$OCH_2CH_2O$—)
4.10 (2H: —P(O)$OCH_2CH_2$—)

Reference Example 2

(1) In a 1-L, four-necked flask equipped with a thermometer and a receiver for removing low-boiling substances, 500 g (0.92 mol) of a compound of the formula:

$$C_4F_9(CH_2CF_2)(CF_2CF_2)(CH_2CH_2)I \text{ (99 GC %)}$$

and 213 g (1.84 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 107 g (0.92 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 138 to 142° C. The distillate fraction was washed with water, thereby obtaining 407 g (yield: 79%) of a purified reaction product (98 GC %).

The results of $^1$H-NMR and $^{19}$F-NMR confirmed that the resulting purified reaction product was a compound represented by the following formula:

$$C_4F_9(CH_2CF_2)(CF_2CF_2)(CH_2CH_2)P(O)(OCH_2CH_3)_2$$

(2) In a 1-L, four-necked flask equipped with a thermometer and a condenser, 300 g (0.53 mol) of the obtained phosphonic acid diester of the formula:

$$C_4F_9(CH_2CF_2)(CF_2CF_2)(CH_2CH_2)P(O)(OCH_2CH_3)_2$$
(96 GC %)

and 300 g of about 35% concentrated hydrochloric acid were charged, and the mixture was stirred at 100° C. for 12 hours. After cooling, filtration under reduced pressure was performed to thereby collect 287 g of solid matters. The solid matters were washed with water and filtrated again, further followed by acetone washing and filtration, thereby obtaining 240 g (0.49 mol; yield: 93%) of the target product.

The results of $^1$H-NMR and $^{19}$F-NMR confirmed that the resulting product was the target compound (polyfluoroalkylphosphonic acid B; MW: 492, F content: 57.9 wt. %) represented by the following formula:

$$C_4F_9(CH_2CF_2)(CF_2CF_2)(CH_2CH_2)P(O)(OH)_2$$

Example 2

In Example 1, 99 g (0.20 mol) of the polyfluoroalkylphosphonic acid B obtained in Reference Example 2 (2) and 201 g (0.40 mol) of PEG-a were used, thereby obtaining 280 g (recovery rate: 93%) of a light yellow wax-like reaction mixture (F content: 18.5 wt. %).

The obtained reaction mixture was isolated by preparative liquid chromatography, and the composition of the isolated product was confirmed by $^{19}$F-NMR and $^1$H-NMR. As a result, the weight ratio of PEG-a, product IIa, and product IIb was 50/47/3.

Product IIa (m=about 12):

$$C_4F_9(CH_2CF_2)(CF_2CF_2)(CH_2CH_2)P(O)$$
$$[O(CH_2CH_2O)_mCH_3](OH)$$

Product IIb (m=about 12):

$$C_4F_9(CH_2CF_2)(CF_2CF_2)(CH_2CH_2)P(O)$$
$$[O(CH_2CH_2O)_mCH_3]_2$$

Reference Example 3

(1) In a 1-L capacity, four-necked flask equipped with a thermometer and a receiver for removing low-boiling substances, 500 g (0.76 mol) of a compound of the formula: $C_2F_5(CH_2CF_2)(CF_2CF_2)_3(CH_2CH_2)I$ (97 GC %), and 176 g (1.52 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 88 g (0.76 mol) per batch, and the mixture was stirred for 18 hours in total.

After the reaction was completed, the reaction mixture was subjected to simple distillation under reduced pressure at an internal pressure of 0.2 kPa, an internal temperature of 160 to 170° C., and an overhead temperature of 150 to 155° C. The distillate fraction was washed with water, thereby obtaining 395 g (yield: 77%) of a purified reaction product (96 GC %).

The results of $^1$H-NMR and $^{19}$F-NMR confirmed that the resulting purified reaction product was a compound represented by the following formula:

$$C_2F_5(CH_2CF_2)(CF_2CF_2)_3(CH_2CH_2)P(O)$$
$$(OCH_2CH_3)_2$$

(2) In a 1-L capacity, four-necked flask equipped with a thermometer and a condenser, 300 g (0.44 mol) of the polyfluoroalkylphosphonic acid diester of the formula: $C_2F_5(CH_2CF_2)(CF_2CF_2)_3(CH_2CH_2)P(O)(OCH_2CH_3)_2$ (96 GC %) obtained in step (1) above, and 300 g of about 35% concentrated hydrochloric acid were charged, and the mixture was stirred at 100° C. for 12 hours. After cooling, filtration under reduced pressure was performed to thereby collect 276 g of solid matters. The solid matters were washed with water and filtrated again, further followed by acetone washing and filtration, thereby obtaining 237 g (0.40 mol; yield: 90%) of the target product.

The results of $^1$H-NMR and $^{19}$F-NMR confirmed that the resulting reaction product was the target compound (polyfluoroalkylphosphonic acid C; MW: 592, F content: 61.0 wt. %) represented by the following formula:

$$C_2F_5(CH_2CF_2)(CF_2CF_2)_3(CH_2CH_2)P(O)(OH)_2$$

Example 3

In Example 1, 112 g (0.19 mol) of the polyfluoroalkylphosphonic acid C obtained in Reference Example 3 (2) and 188 g (0.38 mol) of PEG-a were used, thereby obtaining 281 g (recovery rate: 94%) of a light yellow wax-like reaction mixture (F content: 21.9 wt. %).

The obtained reaction mixture was isolated by preparative liquid chromatography, and the composition of the isolated product was confirmed by $^{19}$F-NMR and $^1$H-NMR. As a result, the weight ratio of PEG-a, product IIIa, and product IIIb was 48/48/4.

(m=about 12):

$$C_2F_5(CH_2CF_2)(CF_2CF_2)_3(CH_2CH_2)P(O)$$
$$[O(CH_2CH_2O)_mCH_3](OH) \qquad \text{Product IIIa}$$

(m=about 12):

$$C_2F_5(CH_2CF_2)(CF_2CF_2)_3(CH_2CH_2)P(O)$$
$$[O(CH_2CH_2O)_mCH_3]_2 \qquad \text{Product IIIb}$$

Reference Example 4

(1) In a 1-L, four-necked flask equipped with a thermometer and a receiver for removing low-boiling substances, 500 g (0.90 mol) of a compound of the formula:

$$C_2F_5(CH_2CF_2)(CF_2CF_2)_2(CH_2CH_2)I \text{ (97 GC %)}$$

and 208 g (1.80 mol) of triethyl phosphite P(OC$_2$H$_5$)$_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 104 g (0.90 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 138 to 142° C. The distillate fraction was washed with water, thereby obtaining 397 g (yield: 78%) of a purified reaction product (97 GC %).

The results of $^1$H-NMR and $^{19}$F-NMR confirmed that the resulting purified reaction product was a compound represented by the following formula:

C$_2$F$_5$(CH$_2$CF$_2$)(CF$_2$CF$_2$)$_2$(CH$_2$CH$_2$)P(O)(OCH$_2$CH$_3$)$_2$ (2) In a 1-L, four-necked flask equipped with a thermometer and a condenser, 300 g (0.52 mol) of the obtained phosphonic acid diester of the formula:

C$_2$F$_5$(CH$_2$CF$_2$)(CF$_2$CF$_2$)$_2$(CH$_2$CH$_2$)P(O)(OCH$_2$CH$_3$)$_2$ (95 GC %)

and 300 g of about 35% concentrated hydrochloric acid were charged, and the mixture was stirred at 100° C. for 12 hours. After cooling, filtration under reduced pressure was performed to thereby collect 271 g of solid matters. The solid matters were washed with water and filtrated again, further followed by acetone washing and filtration, thereby obtaining 235 g (0.48 mol; yield: 92%) of the target product.

The results of $^1$H-NMR and $^{19}$F-NMR confirmed that the resulting product was the target compound (polyfluoroalkylphosphonic acid D; MW: 492, F content: 57.9 wt. %) represented by the following formula:

C$_2$F$_5$(CH$_2$CF$_2$)(CF$_2$CF$_2$)$_2$(CH$_2$CH$_2$)P(O)(OH)$_2$

Example 4

In Example 1, 99 g (0.20 mol) of the polyfluoroalkylphosphonic acid D obtained in Reference Example 4 (2) and 201 g (0.40 mol) of PEG-a were used, thereby obtaining 276 g (recovery rate: 92%) of a light yellow wax-like reaction mixture (F content: 18.8 wt. %).

The obtained reaction mixture was isolated by preparative liquid chromatography, and the composition of the isolated product was confirmed by $^{19}$F-NMR and $^1$H-NMR. As a result, the weight ratio of PEG-a, product IVa, and product IVb was 50/47/3.
(m=about 12):

C$_2$F$_5$(CH$_2$CF$_2$)(CF$_2$CF$_2$)$_2$(CH$_2$CH$_2$)P(O)[O(CH$_2$CH$_2$O)$_m$CH$_3$](OH)   Product IVa (m=about 12):

C$_2$F$_5$(CH$_2$CF$_2$)(CF$_2$CF$_2$)$_2$(CH$_2$CH$_2$)P(O)[O(CH$_2$CH$_2$O)$_m$CH$_3$]$_2$   Product IVb Reference Example 5

(1) In a 1-L capacity, four-necked flask equipped with a thermometer and a receiver for removing low-boiling substances, 500 g (0.88 mol) of a compound of the formula: C$_2$F$_5$(CH$_2$CF$_2$)(CF$_2$CF$_2$)$_2$(CH$_2$CH$_2$)$_2$I (97 GC %), and 204 g (1.76 mol) of triethyl phosphite P(OC$_2$H$_5$)$_3$ were charged, and the mixture was stirred at 155° C. At this time, to remove the by-product, i.e., ethyl iodide, from the reaction system, nitrogen gas was bubbled into the reaction solution using a slender tube. A slight amount of reaction solution was taken and subjected to gas chromatography analysis to confirm the remaining amount of triethyl phosphite. Thereafter, triethyl phosphite was further added in four batches in an amount of 104 g (0.90 mol) per batch, and the mixture was stirred for 18 hours in total.

After the reaction was completed, the reaction mixture was subjected to simple distillation under reduced pressure at an internal pressure of 0.2 kPa, an internal temperature of 145 to 155° C., and an overhead temperature of 140 to 142° C. The distillate fraction was washed with water, thereby obtaining 410 g (yield: 79%) of a purified reaction product (97 GC %).

The results of $^1$H-NMR and $^{19}$F-NMR confirmed that the resulting purified reaction product was a compound represented by the following formula:

C$_2$F$_5$(CH$_2$CF$_2$)(CF$_2$CF$_2$)$_2$(CH$_2$CH$_2$)$_2$P(O)(OCH$_2$CH$_3$)$_2$ (2) In a 1-L capacity, four-necked flask equipped with a thermometer and a condenser, 300 g (0.51 mol) of the polyfluoroalkylphosphonic acid diester of the formula: C$_2$F$_5$(CH$_2$CF$_2$)(CF$_2$CF$_2$)$_2$(CH$_2$CH$_2$)$_2$P(O)(OCH$_2$CH$_3$)$_2$ (97 GC %) obtained in step (1) above, and 300 g of about 35% concentrated hydrochloric acid were charged, and the mixture was stirred at 100° C. for 12 hours. After cooling, filtration under reduced pressure was performed to thereby collect 269 g of solid matters. The solid matters were washed with water and filtrated again, further followed by acetone washing and filtration, thereby obtaining 240 g (0.46 mol; yield: 90%) of the target product.

The results of $^1$H-NMR and $^{19}$F-NMR confirmed that the resulting reaction product was the target compound (polyfluoroalkylphosphonic acid E; MW: 553, F content: 51.5 wt. %) represented by the following formula:

C$_2$F$_5$(CH$_2$CF$_2$)(CF$_2$CF$_2$)$_2$(CH$_2$CH$_2$)$_2$P(O)(OH)$_2$

Example 5

In Example 1, 107 g (0.19 mol) of the polyfluoroalkylphosphonic acid E obtained in Reference Example 5 (2) and 193 g (0.39 mol) of PEG-a were used, thereby obtaining 272 g (recovery rate: 91%) of a light yellow wax-like reaction mixture (F content: 18.3 wt. %).

The obtained reaction mixture was isolated by preparative liquid chromatography, and the composition of the isolated product was confirmed by $^{19}$F-NMR and $^1$H-NMR. As a result, the weight ratio of PEG-a, product Va, and product Vb was 49/48/3.
(m=about 12):

C$_2$F$_5$(CH$_2$CF$_2$)(CF$_2$CF$_2$)$_2$(CH$_2$CH$_2$)$_2$P(O)[O(CH$_2$CH$_2$O)$_m$CH$_3$](OH)   Product Va (m=about 12):

C$_2$F$_5$(CH$_2$CF$_2$)(CF$_2$CF$_2$)$_2$(CH$_2$CH$_2$)$_2$P(O)[O(CH$_2$CH$_2$O)$_m$CH$_3$]$_2$   Product Vb Reference Example 6

(1) In a 1-L, four-necked flask equipped with a thermometer and a receiver for removing low-boiling substances, 500 g (1.12 mol) of a compound of the formula:

C$_2$F$_5$(CH$_2$CF$_2$)(CF$_2$CF$_2$)(CH$_2$CH$_2$)I (98 GC %)

and 259 g (2.24 mol) of triethyl phosphite $P(OC_2H_5)_3$ were charged, and the mixture was stirred at 155° C. At this time, to remove the by-product, i.e., ethyl iodide, from the reaction system, nitrogen gas was bubbled into the reaction solution using a small tube. A slight amount of reaction solution was taken and subjected to gas chromatographic analysis to confirm the remaining amount of triethyl phosphite. Thereafter, triethyl phosphite was further added in four batches in an amount of 130 g (1.12 mol) per batch, and the mixture was stirred for 18 hours in total.

After the reaction was completed, the reaction mixture was subjected to simple distillation under reduced pressure at an internal pressure of 0.2 kPa, an internal temperature of 130 to 140° C., and an overhead temperature of 128 to 131° C. The distillate fraction was washed with water, thereby obtaining 405 g (yield: 79%) of a purified reaction product (98 GC %).

The results of $^1$H-NMR and $^{19}$F-NMR confirmed that the resulting purified reaction product was a compound represented by the following formula:

$$C_2F_5(CH_2CF_2)(CF_2CF_2)(CH_2CH_2)P(O)(OCH_2CH_3)_2$$

(2) In a 1-L, four-necked flask equipped with a thermometer and a condenser, 300 g (0.63 mol) of the obtained phosphonic acid diester of the formula:

$$C_2F_5(CH_2CF_2)(CF_2CF_2)(CH_2CH_2)P(O)(OCH_2CH_3)_2$$
(94 GC %)

and 300 g of about 35% concentrated hydrochloric acid were charged, and the mixture was stirred at 100° C. for 12 hours. After cooling, filtration under reduced pressure was performed to thereby collect 262 g of solid matters. The solid matters were washed with water and filtrated again, further followed by acetone washing and filtration, thereby obtaining 229 g (0.59 mol; yield: 93%) of the target product.

The results of $^1$H-NMR and $^{19}$F-NMR confirmed that the resulting product was the target compound (polyfluoroalkylphosphonic acid F; MW: 392, F content: 53.3 wt. %) represented by the following formula:

$$C_2F_5(CH_2CF_2)(CF_2CF_2)(CH_2CH_2)P(O)(OH)_2$$

Example 6

In Example 1, 85 g (0.22 mol) of the polyfluoroalkylphosphonic acid F obtained in Reference Example 6 (2) and 215 g (0.43 mol) of PEG-a were used, thereby obtaining 274 g (recovery rate: 91%) of a light yellow wax-like reaction mixture (F content: 14.9 wt. %).

The obtained reaction mixture was isolated by preparative liquid chromatography, and the composition of the isolated product was confirmed by $^{19}$F-NMR and $^1$H-NMR. As a result, the weight ratio of PEG-a, product VIa, and product VIb was 49/48/3.

(m=about 12):

$$C_2F_5(CH_2CF_2)(CF_2CF_2)(CH_2CH_2)P(O)\\[O(CH_2CH_2O)_mCH_3](OH) \quad \text{Product VIa}$$

(m=about 12):

$$C_2F_5(CH_2CF_2)(CF_2CF_2)(CH_2CH_2)P(O)\\[O(CH_2CH_2O)_mCH_3]_2 \quad \text{Product VIb}$$

Example 7

In Example 1, 60 g (0.12 mol) of the polyfluoroalkylphosphonic acid B obtained in Reference Example 2 (2) and 240 g (0.48 mol) of PEG-a were used, thereby obtaining 274 g (recovery rate: 91%) of a light yellow wax-like reaction mixture (F content: 11.3 wt. %).

The obtained reaction mixture was isolated by preparative liquid chromatography, and the composition of the isolated product was confirmed by $^{19}$F-NMR and $^1$H-NMR. As a result, the weight ratio of PEG-a, product IIa, and product IIb was 50/3/47.

(m=about 12):

$$C_4F_9(CH_2CF_2)(CF_2CF_2)(CH_2CH_2)P(O)\\[O(CH_2CH_2O)_mCH_3](OH) \quad \text{Product IIa}$$

(m=about 12):

$$C_4F_9(CH_2CF_2)(CF_2CF_2)(CH_2CH_2)P(O)\\[O(CH_2CH_2O)_mCH_3]_2 \quad \text{Product IIb}$$

Example 8

In Example 1, 35 g (0.07 mol) of the polyfluoroalkylphosphonic acid B obtained in Reference Example 2 (2) and 265 g (0.15 mol) of polyethyleneglycol monomethyl ether [PEG-b] (Uniox M-2000, produced by NOF Corporation; MW=1,816, m=about 45) of the formula:

$$HO(CH_2CH_2O)_mCH_3$$

were used, thereby obtaining 280 g (recovery rate: 93%) of a light yellow wax-like reaction mixture (F content: 6.6 wt. %).

The obtained reaction mixture was isolated by preparative liquid chromatography, and the composition of the isolated product was confirmed by $^{19}$F-NMR and $^1$H-NMR. As a result, the weight ratio of PEG-b, product VIIa, and product VIIb was 48/48/4.

(m=about 45):

$$C_4F_9(CH_2CF_2)(CF_2CF_2)(CH_2CH_2)P(O)\\[O(CH_2CH_2O)_mCH_3](OH) \quad \text{Product VIIa}$$

(m=about 45):

$$C_4F_9(CH_2CF_2)(CF_2CF_2)(CH_2CH_2)P(O)\\[O(CH_2CH_2O)_mCH_3]_2 \quad \text{Product VIIb}$$

Example 9

In Example 1, 75 g (0.15 mol) of the polyfluoroalkylphosphonic acid B obtained in Reference Example 2 (2) and 225 g (0.29 mol) of polypropyleneglycol monobutyl ether [PPG-a] (NEWPOL M-30, produced by Sanyo Chemical Industries, Ltd.; MW=786, m=about 14) of the formula:

$$HO[CH_2CH(CH_3)O]_mC_4H_9$$

were used, thereby obtaining 280 g (recovery rate: 93%) of a light yellow wax-like reaction mixture (F content: 14.0 wt. %).

The obtained reaction mixture was isolated by preparative liquid chromatography, and the composition of the isolated product was confirmed by $^{19}$F-NMR and $^1$H-NMR. As a result, the weight ratio of PEG-a, product VIIIa, and product VIIIb was 48/49/3.

(m=about 14):

$$C_4F_9(CH_2CF_2)(CF_2CF_2)(CH_2CH_2)P(O)\{O[CH_2CH\\(CH_3)O]_mC_4H_9\}(OH) \quad \text{Product VIIIa}$$

(m=about 14):

$$C_4F_9(CH_2CF_2)(CF_2CF_2)(CH_2CH_2)P(O)\{O[CH_2CH\\(CH_3)O]_mC_4H_9\}_2 \quad \text{Product VIIIb}$$

Example 10

In Example 1, 122 g (0.22 mol) of the polyfluoroalkylphosphonic acid B obtained in Reference Example 2 (2) and 178 g (0.43 mol) of polypropyleneglycol [PPG-b] (Uniox D-400, produced by NOF Corporation; MW=418, m=about 8) of the formula:

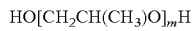

were used, thereby obtaining 281 g (recovery rate: 94%) of a light yellow wax-like reaction mixture (F content: 22.6 wt. %).

The obtained reaction mixture was isolated by preparative liquid chromatography, and the composition of the isolated product was confirmed by $^{19}$F-NMR and $^{1}$H-NMR. As a result, the weight ratio of PEG-b, product IXa, product IXb, and product IXc was 48/46/3/3.

(m=about 8):

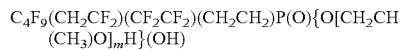   Product IXa (m=about 8):

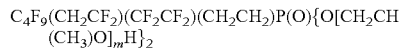   Product IXb (m=about 8):

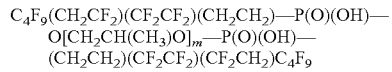   Product IXc

Example 11

A mold-releasing agent aqueous solution comprising 0.5 wt. % of the polyfluoroalkylphosphonic acid oxyalkylene ester-containing reaction mixture obtained in Example 1, 99.45 wt. % of ion exchange water, and 0.05 wt. % of triethylamine was prepared. Using the mold-releasing agent aqueous solution, mold releasability was evaluated by the following two measurement methods. The results were such that the mold releasability was 6.0 N, and the mold release life was 10 times.

Evaluation of Mold Releasability and Mold Release Life

Polyurethane prepolymer (100 parts by weight; Coronate C-4090, manufactured by Nippon Polyurethane Industry Co., Ltd.), which had been heated to 80° C., and 12.8 parts by weight of methylene-bis-o-chloroaniline curing agent (Iharacuamine MT, manufactured by Ihara Chemical Industry Co., Ltd.), which had been heat-melted, were mixed by stirring without forming air bubbles. The mixture was poured into an aluminum mold (diameter: 45 mm, depth: 50 mm) to which the above mold-releasing agent aqueous solution had been applied by spraying, and which had been preheated to 80° C. A hook was stood in the center of the space of the mold for removing the cured molded product. After heat-curing at 120° C. for 1 hour, the molded product was taken out from the mold by pulling the hook. The mold release load required to pull the hook was regarded as mold releasability. After the mold releasability was thus determined, mold release life was determined by measuring how many times a one-time application of the mold-releasing agent aqueous solution allowed mold releasing at a mold release load of 50 N or less.

Comparative Example

In Example 1, mold releasability and mold release life were evaluated without applying the mold-releasing agent aqueous solution. The results were such that the mold releasability could not be measured because the molded product was not removed from the mold, and the mold release life was therefore 0 times.

Examples 12 to 20

In Example 11, as the polyfluoroalkylphosphonic acid oxyalkylene ester-containing reaction mixture, each of the polyfluoroalkylphosphonic acid oxyalkylene ester-containing reaction mixtures obtained in Examples 2 to 10 was used, and the same measurement was carried out. The following table shows the obtained results.

TABLE

| Example | Phosphonic acid ester mixture | Mold releasability (N) | Mold release life (Time) |
|---|---|---|---|
| 12 | Example 2 | 4.5 | 10 |
| 13 | Example 3 | 5.0 | 11 |
| 14 | Example 4 | 5.5 | 9 |
| 15 | Example 5 | 5.5 | 9 |
| 16 | Example 6 | 6.0 | 8 |
| 17 | Example 7 | 7.0 | 8 |
| 18 | Example 8 | 10.0 | 7 |
| 19 | Example 9 | 8.0 | 9 |
| 20 | Example 10 | 5.0 | 10 |

Example 21

In Example 12 using the polyfluoroalkylphosphonic acid oxyalkylene ester-containing reaction mixture obtained in Example 2, the dispersion medium was changed to 85.00 wt. % of ion exchange water and 14.45 wt. % of ethanol, and the same measurement was carried out. The results were such that the mold releasability was 5.0 N, and the mold release life was 11 times.

Example 22

In Example 12 using the polyfluoroalkylphosphonic acid oxyalkylene ester-containing reaction mixture obtained in Example 2, the dispersion medium was changed to 86.00 wt. % of 1,4-bis(trifluoromethyl)benzene and 13.45 wt. % of isopropanol, and the same measurement was carried out. The results were such that the mold releasability was 5.0 N, and the mold release life was 10 times.

Meanwhile, a mold-releasing agent aqueous solution comprising 0.5 wt. % of a compound of the formula: $CF_3(CF_2)_7CH_2CH_2P(O)(OH)_2$, 99.30 wt. % of ion exchange water, and 0.20 wt. % of triethylamine was prepared, and the same measurement as in Example 11 was carried out. The results were such that the mold releasability was 7.0 N, and the mold release life was 12 times.

The invention claimed is:

1. A polyfluoroalkylphosphonic acid oxyalkylene ester represented by the general formula:

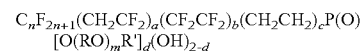   [I]

wherein RO is a linear or branched oxyalkylene group having 2 to 6 carbon atoms, R' is a hydrogen atom, an alkyl group having 1 to 20 carbon atoms, or aralkyl group, n is an integer of 1 to 6, a is an integer of 1 to 4, b is an integer of 1 to 3, c is an integer of 1 to 3, d is an integer of 1 or 2, and m is an integer of 1 to 100.

2. The polyfluoroalkylphosphonic acid oxyalkylene ester according to claim 1, wherein the polyfluoroalkylphosphonic acid oxyalklene ester is a mixture of polyfluoroalkylphosphonic acid monooxyalkylene ester represented by the general formula:

$$C_nF_{2n+1}(CH_2CF_2)_a(CF_2CF_2)_b(CH_2CH_2)_cP(O)[O(RO)_mR'](OH)$$

and a polyfluoroalkylphosphonic acid bis(oxyalkylene)ester represented by the formula:

$$C_nF_{2n+1}(CH_2CF_2)_a(CF_2CF_2)_b(CH_2CH_2)_cP(O)[O(RO)_mR']_2.$$

3. A mold-releasing agent comprising the polyfluoroalkylphosphonic acid oxyalkylene ester according to claim 1 as an active ingredient.

4. A mold-releasing agent comprising the polyfluoroalkylphosphonic acid oxyalkylene ester according to claim 2 as an active ingredient.

5. The mold-releasing agent according to claim 3, further containing a polyalkyleneglycol or monoether thereof.

6. The mold-releasing agent according to claim 3, which is used as an aqueous solution.

7. The mold-releasing agent according to claim 3, which is used as an aqueous dispersion.

8. The mold-releasing agent according to claim 3, which is used as an organic solvent solution.

9. The mold-releasing agent according to claim 3, wherein the polyfluoroalkylphosphonic acid oxyalkylene ester has a solid matters content of 0.01 to 30 wt. %.

10. The mold-releasing agent according to claim 3, which is applied to a forming mold for use.

11. The mold-releasing agent according to claim 4, further containing a polyalkyleneglycol or monoether thereof.

12. The mold-releasing agent according to claim 4, which is used as an aqueous solution.

13. The mold-releasing agent according to claim 4, which is used as an aqueous dispersion.

14. The mold-releasing agent according to claim 4, which is used as an organic solvent solution.

15. The mold-releasing agent according to claim 4, wherein the polyfluoroalkylphosphonic acid oxyalkylene ester has a solid matters content of 0.01 to 30 wt. %.

16. The mold-releasing agent according to claim 4, which is applied to a forming mold for use.

17. A method for producing the polyfluoroalkylphosphonic acid oxyalkylene ester according to claim 2, the method comprising subjecting a polyfluoroalkylphosphonic acid represented by the general formula:

$$C_nF_{2n+1}(CH_2CF_2)_a(CF_2CF_2)_b(CH_2CH_2)_cP(O)(OH)_2 \quad [II]$$

wherein n is an integer of 1 to 6, a is an integer of 1 to 4, b is an integer of 1 to 3, c is an integer of 1 to 3, and a polyalkyleneglycol or monoether thereof represented by the general formula:

$$HO(RO)_mR' \quad [X]$$

wherein RO is a linear or branched oxyalkylene group having 2 to 6 carbon atoms, R' is a hydrogen atom, an alkyl group having 1 to 20 carbon atoms, or aralkyl group, and m is an integer of 1 to 100, to condensation reaction.

18. A method for producing the polyfluoroalkylphosphonic acid oxyalkylene ester represented by the general formula:

$$C_nF_{2n+1}(CH_2CF_2)_a(CF_2CF_2)_b(CH_2CH_2)_cP(O)[O(RO)_mR']_d(OH)_{2-d} \quad [I]$$

wherein RO is a linear or branched oxyalkylene group having 2 to 6 carbon atoms, R' is a hydrogen atom, an alkyl group having 1 to 20 carbon atoms, or aralkyl group, n is an integer of 1 to 6, a is an integer of 1 to 4, b is an integer of 1 to 3, c is an integer of 1 to 3, d is an integer of 1 or 2, and m is an integer of 1 to 100, the method comprising subjecting a polyfluoroalkylphosphonic acid represented by the general formula:

$$C_nF_{2n+1}(CH_2CF_2)_a(CF_2CF_2)_b(CH_2CH_2)_cP(O)(OH)_2 \quad [II]$$

wherein n is an integer of 1 to 6, a is an integer of 1 to 4, b is an integer of 1 to 3, c is an integer of 1 to 3, and a polyalkyleneglycol or monoether thereof represented by the general formula:

$$HO(RO)_mR' \quad [X]$$

wherein RO is a linear or branched oxyalkylene group having 2 to 6 carbon atoms, R' is a hydrogen atom, an alkyl group having 1 to 20 carbon atoms, or aralkyl group, and m is an integer of 1 to 100, to condensation reaction.

19. A method for producing the polyfluoroalkylphosphonic acid oxyalkylene ester according to claim 18, wherein the polyfluoroalkylphosphonic acid oxyalklene ester is a mixture of polyfluoroalkylphosphonic acid monooxyalkylene ester represented by the general formula:

$$C_nF_{2n+1}(CH_2CF_2)_a(CF_2CF_2)_b(CH_2CH_2)_cP(O)[O(RO)_mR'](OH)$$

and a polyfluoroalkylphosphonic acid bis(oxyalkylene)ester represented by the formula:

$$C_nF_{2n+1}(CH_2CF_2)_a(CF_2CF_2)_b(CH_2CH_2)_cP(O)[O(RO)_mR']_2.$$

* * * * *